US009439929B2

(12) United States Patent
Song et al.

(10) Patent No.: US 9,439,929 B2
(45) Date of Patent: *Sep. 13, 2016

(54) TREATMENT OF GRAFT-VERSUS-HOST DISEASE

(75) Inventors: Sun Uk Song, Incheon (KR); Moon Hee Lee, Incheon (KR); Chul Soo Kim, Seoul (KR)

(73) Assignee: INHA-INDUSTRY PARTNERSHIP INSTITUTE, Incheon (KR)

( * ) Notice: Subject to any disclaimer, the term of this patent is extended or adjusted under 35 U.S.C. 154(b) by 1900 days.

This patent is subject to a terminal disclaimer.

(21) Appl. No.: 12/127,734

(22) Filed: May 27, 2008

(65) Prior Publication Data

US 2008/0292600 A1 Nov. 27, 2008
US 2016/0166614 A9 Jun. 16, 2016

Related U.S. Application Data

(63) Continuation-in-part of application No. 11/471,684, filed on Jun. 19, 2006, now Pat. No. 7,781,211.

(60) Provisional application No. 60/940,349, filed on May 25, 2007, provisional application No. 60/595,254, filed on Jun. 17, 2005.

(51) Int. Cl.
| | |
|---|---|
| *A01N 63/00* | (2006.01) |
| *A61K 35/28* | (2015.01) |
| *A61K 38/20* | (2006.01) |
| *C12N 5/0775* | (2010.01) |
| *A61K 35/17* | (2015.01) |
| *A61K 35/12* | (2015.01) |

(52) U.S. Cl.
CPC ............... *A61K 35/28* (2013.01); *A61K 35/17* (2013.01); *A61K 38/2066* (2013.01); *C12N 5/0663* (2013.01); *A61K 2035/122* (2013.01); *A61K 2035/124* (2013.01)

(58) Field of Classification Search
None
See application file for complete search history.

(56) References Cited

U.S. PATENT DOCUMENTS

| | | | | |
|---|---|---|---|---|
| 5,426,098 | A * | 6/1995 | Carlino | 514/8.9 |
| 5,690,926 | A | 11/1997 | Hogan | |
| 5,750,376 | A * | 5/1998 | Weiss et al. | 435/69.52 |
| 5,827,742 | A | 10/1998 | Scadden | |
| 6,082,364 | A | 7/2000 | Balian et al. | |
| 6,328,960 | B1 * | 12/2001 | McIntosh et al. | 424/93.71 |
| 7,781,211 | B2 | 8/2010 | Song | |
| 2003/0180269 | A1 | 9/2003 | Hariri | |
| 2005/0142119 | A1 | 6/2005 | Seshi | |
| 2005/0239897 | A1 * | 10/2005 | Pittenger et al. | 514/569 |
| 2006/0286669 | A1 | 12/2006 | Song | |
| 2008/0292601 | A1 | 11/2008 | Song | |

FOREIGN PATENT DOCUMENTS

JP 2002-506831 W 3/2002
WO WO 99/47163 A2 9/1999

OTHER PUBLICATIONS

Seaberg RM and van der Kooy D. 2003. Stem and progenitor cells: the premature desertion of rigorous definitions. Trends Neurosci 26: 125-131.*
Ryan JM et al. 2005. Mesenchymal stem cells avoid allogeneic rejection. J Inflamm 2:8.*
Pittenger MF et al. 1999. Multilineage Potential of Adult Human Mesenchymal Stem Cells. Science 284: 143-147, plus supplemental material available online at http://www.sciencemag.org/site/feature/data/983855.xhtml.*
Hung S-C et al. 2002. Isolation and Characterization of Size-Sieved Stem Cells from Human Bone Marrow. Stem Cells 20: 249-258.*
Jones, et al., "Computed Tomography of Gastrointestinal Inflammation after Bone Marrow Transplantation," American J Roentgenology, 146:891-695, 1986.
Fujii, et al., "Hepatic graft-versus-host disease presenting as an acute hepatitis after allogeneic peripheral blood stem cell transplantation," Bone Marrow Transplantation, 27:1007-1010, 2001.
Lim, et al., "Mesenchymal stromal cells for steroid-refractory acute graft-versus-host disease: a report of two cases," Int J Hematol, 92:204-207, 2010.
Jeon, et al., "Characterization of mouse clonal mesenchymal stem cell lines established by subfractionation culturing method," World J Stem Cells, 3(8):70-82, 2011.
Qu-Peterson et al., "Identification of a novel population of muscle stem cells in mice: Potential for muscle regeneration," The J. of Cell Biology, Rockefeller University Press, 157(5):851-864, May 27, 2002.
Lee et al., "Clonal isolation of muscle-derived cells capable of enhancing muscle regeneration and bone healing," The J. of Cell Biology, Rockefeller University Press, 150(5):1085-1099, Sep. 4, 2000.
Prockop et al., "Isolation and characterization of rapidly self-renewing stem cells from cultures of human marrow stromal cells," Cytotherapy, Isis Medical Media, 3(5):393-396, Jan. 1, 2001.
Colter et al., "Rapid expansion of recycling stem cells in cultures of plastic-adherent cells from human bone marrow," Proceedings of the National Academy of Sciences of USA, National Academy of Science, 97(7):3213-3218, Mar. 28, 2000.
Lu et al., "Can bone marrow-derived stem cells differentiate into functional neurons?" Experimental neurology, Academic Press, 193(2):273-278, Jun. 1, 2005.
Pittenger et al., "Multilineage potential of adult human mesenchymal stem cells," Science, 284(5411):143-147, Apr. 2, 1999.
Song et al., "Variations of clonal marrow stem cell lines established from human bone marrow in surface epitopes, differentiation potential, gene expression, and cytokine secretion," Stem Cells and Development, 17(3):451-461, Jun. 2008.

(Continued)

*Primary Examiner* — Lora E Barnhart Driscoll
(74) *Attorney, Agent, or Firm* — Joseph Hyosuk Kim; JHK Law

(57) ABSTRACT

This present application describes a therapeutic agent for treating acute or chronic graft-versus-host disease using clonal marrow stem cells (cMSCs) as active ingredient.

18 Claims, 5 Drawing Sheets

(56) References Cited

OTHER PUBLICATIONS

Woodbury et al., "Adult Rat and Human Bone Marrow Stromal Cells Differentiate Into Neurons", Journal of Neuroscience Research (2000), 61:364-370.

Sato et al., "Human mesenchymal stem cells xenografted directly to rat liver are differentiated into human hepatocytes without fusion", Blood (2005), 106: 756-763.

Igaku No Ayumi, 2005, Additional volume (September), Recent Advances on Treatment Method No. 31, Application for hematopoietic stem cell transplantation of mesenchymal stem cells (MSC), pp. 564-567.

Journal of Japanese society or laboratory hematology, 2007. vol. 8, No. 1 pp. 54-61.

Bianco et al., "The meaning, the sense and the significance: translating the science of mesenchymal stem cells into medicine," Nature Medicine vol. 19, No. 1, 2013.

Shi et al., Blood, vol. 92, pp, 362-367; 1998.

Gupta, Mol. Cell. Endocrinol. vol. 152, pp. 169-178; 1999.

\* cited by examiner

A  Before Treatment
B  10 days after Treatment
C  1 Month after Treatment
D  3 Months after Treatment

TREATMENT OF GRAFT-VERSUS-HOST DISEASE

CROSS-REFERENCE TO RELATED APPLICATIONS

The present application claims the benefit of priority to U.S. Provisional Patent Application No. 60/940,349, filed May 25, 2007, the contents of which are incorporated by reference herein in their entirety. The present application is also a continuation-in-part application of U.S. patent application Ser. No. 11/471,684, filed Jun. 19, 2006, now U.S. Pat. No. 7,781,211, patented Aug. 24, 2010, which claims the benefit of priority to U.S. Provisional Patent Application No. 60/595,254, filed Jun. 17, 2005.

BACKGROUND OF THE INVENTION

1. Field of the Invention

The present invention relates to a therapeutic agent for treating acute or chronic graft-versus-host disease. The present invention also relates to a therapeutic agent for treating acute or chronic graft-versus-host disease that contains mesenchymal stem cells as an active ingredient.

2. General Background and State of the Art

Graft-versus-host disease (GVHD) refers to a disease wherein the body of the patient has an immune reaction to the donor's peripheral blood or the T lymphocytes in the bone marrow that are injected during homogeneous transplantation. Namely, it is a disease that is induced by living lymphocytes which were transfused causing an immune reaction that leads to problems in liver function, skin lesions, jaundice, diarrhea, fever, pancytopenia, and so on, and in severe cases patient death.

Graft-versus-host disease can be classified largely into acute graft-versus-host disease (aGVHD) and chronic graft-versus-host disease (cGVHD). cGVHD is the most major and common side effect, occurring in 20%-70% of patients living past 100 days following blood and marrow progenitor cell transplantation, and a major cause of death following transplantation. Because cGVHD and aGVHD are not successive diseases, aGVHD requires a different approach and cGVHD is becoming the bigger problem due to developments in blood and marrow progenitor cell transplantation therapeutic methods.

cGVHD in the case of homogenous transplantations, occurs usually 4-6 months following transplantation and its occurrence within 80 days or after 1 year is uncommon. Accordingly, it can be seen that a homogeneous reaction is a major prerequisite for causing cGVHD and the pathogenesis of cGVHD goes through a long incubation period or the effect on the target organ shows up slowly. Various problems in the function of the thymus gland are being discovered in the cGVHD, and it is thought that if normal thymus glands are not removed through damage caused by treatment prior to transplantation or isoantigen/autoantigen through peripheral mechanisms, pathological graft T cells increase as a reaction, and this type of pathological CD positive T cells, as a Th2 immunological reaction, cause immune deficiencies similar to auto immune diseases including cytolytic attack, secretion of inflamed fibrosis cytokine, B cell activation, and damage to target organs through formation of auto antibodies.

Clinical symptoms of cGVHD include changes in the skin such as erythema, dryness, itchiness, pigmentation change, and maculopapular rashes; changes in hair such as thinning of hair and loss of hair, and changes in the mouth such as inflamed gums, mucositis, and lip atrophy. Aside from the various lesions appearing on the eyes, reproductive organs, liver, lungs, gastrointestinal tracts, fascia, skeletal system, serous membranes, and so forth.

While cGVHD is generally defined as GVHD that occurs after 100 days following bone marrow transplantation, the manifested conditions are more important to the diagnosis than the manifested time period. In accordance with the manifested time period of the symptoms, classification can be made between a progressive onset in which aGVHD not having been cured since occurrence shifts to cGVHD, a quiescent onset in which cGVHD appears after aGVHD has been fully cured, and de novo in which it occurs without prior appearance of aGVHD. The morbidity and death rate is highest in the progressive onset, next is quiescent onset, and it is lowest in the case of de novo. As for manifested conditions, in many cases lichenous shaped rashes in the skin and mucous coat of the mouth are the first symptoms, and while it may appear on the same parts as in aGVHD, the lesions are papulous, invasive, and covered with white scales. When compared with aGVHD from a pathological histology perspective, while legions of satellite cell necrosis can still be found, the lymphocyte infiltration shows an over consolidated band. Aside from that, the gall bladder duct is diminished, and while bile accumulation can be seen, because there may be cases in which it may be mixed with legions related to the medication or viral hepatitis, there may be cases in which it is difficult to differentiate from cGVHD.

In the case of cGVHD, because immune functions are already decreased, there is fear of serious infection during treatment, and a new effective treatment with little side effect from the treatment is keenly needed. In relation to this, many researches are being reported that state there is ability for mesenchymal stem cells to be differentiated into many organ cells and that graft-versus-hot reactions can be improved by suppressing T cells.

While mesenchymal stem cells can be propagated in an undifferentiated situation as primordial cells of the original mesoderm and be separated from various organs such as bone marrow, fat tissue, liver, tendon, synovial membrane, and umbilical cord, a single marker that can precisely define it as a mesenchymal stem cell is not in existence. However, CD14, CD34, and CD45 are well known as markers for bone marrow and SH-2(CD105), SH-3(CD73), SH-4, and Th7-1 are well known as markers for mesenchyma. Mesenchymal stem cells or mesenchymal stromal cells (MSC) express major histocompatibility complex (MHC) class 1, and MHC class can induce manifestation through interferon gamma (IFN-γ), and because it does not manifest FAS or FAS L(CD40) type costimulatory molecules, it does not induce immunological reactions, and is free from cytolysis due to cytotoxic T lymphocytes (CTL) and natural killer (NK) cells. In addition, while mesenchymal stem cells suppress proliferation of T cells through density reliance at time of mixed lymphocyte reaction (MLR) and suppress proliferation of B cells as well as formation of immunoglobulin, it is known that MHC compatibility is not a necessity for MSC immune suppression. In addition, it is known that there is no change in the activity of karyotypes or telomerases in the MSC when split 50 times.

However, because MSC that exists in the body is very rare, development of technology that isolates it is important. Currently, density gradient centrifugal separation, method using monoclonal antibodies specifically for Sca-1 or STRO-1, and separation method according to cell size are known methods for separating MSC. The inventors herein have previously developed an effective MSC separation method (Republic of Korea Public Patent No. 10-0802011) that does not require a particular mechanical device or reagent, and the above method is characterized by the fact that marrow taken from the individual is cultivated, and the cultured upper liquid is further cultivated by repeatedly removing to a new container.

In regards to treatment methods for cGVHD, U.S. Pat. No. 6,544,506 presents a GVHD prevention and treatment method that has as its distinctive feature the removal of cytotoxic T lymphocytes by injecting non-alloreactive anti-cytotoxic lymphocytes in organ transplantation patients. U.S. Pat. No. 6,936,281 describes a GVHD treatment method using mesenchymal stem cells. U.S. Pat. No. 7,173,016 describes a GVHD treatment method that includes the step of injecting adenosine deaminase inhibitors. U.S. Pat. No. 6,328,960 describes a GVHD treatment method that has as its distinctive feature the injection of mesenchymal stem cells in an amount that can lessen the immunological reaction of effector cells against the antigens in the target organ transplantation patient in order to lessen the effector cell's immunological reaction against the alloantigen in the target transplantation patient. U.S. Pat. No. 6,368,636 describes a method of lessening the immunological reaction caused by effector cells, which includes the step of contacting the effector cells with the upper liquid of the mesenchymal stem cells in an injection amount that can reduce the immunological reaction against alloantigen.

Until now, there is no report of a case in which cGVHD has been treated successfully using mesenchymal or marrow stem cells. Accordingly, the inventors herein through attempting to treat cGVHD completed this invention by verifying clinically that mesenchymal or marrow stem cells that were separated using a subfractionation culturing method effectively treats cGVHD.

SUMMARY OF THE INVENTION

A goal of this invention is to provide a therapeutic agent for acute or chronic graft-versus-host disease.

Another goal of this invention is to provide a treatment method for acute or chronic graft-versus-host disease.

In order to achieve the above mentioned goals, this invention provides a therapeutic agent that includes mesenchymal or marrow stem cells for treating acute or chronic graft-versus-host disease.

In addition, this invention also includes a method for treating graft-versus-host disease that includes the step of injecting an effective dose of mesenchymal or marrow stem cells in patients with acute or chronic graft-versus-host disease.

In one aspect, the present invention is directed to a method of inhibiting activity of T-cell from donor marrow in a subject identified as suffering from graft-versus-host disease, comprising administering to the subject in need thereof a therapeutically effective amount of a population of homogeneous clonal marrow stem cells. A dosage of the stem cells per each administration may be between $1\times10^4$ cells/kg body weight to $1\times10^8$ cells/kg weight. The stem cells may be isolated using a subfractionation culturing method. The stem cells may express CD29, CD44, and CD105 cell surface antigens, but not HLA-DR cell surface antigen. The stem cells may express CD29, CD44, CD73 CD90, CD105, and CD166 cell surface antigens but not CD106, CD119, or HLA-DR cell surface antigens. The homogeneous clonal marrow stem cells may secrete interleukin-10 at a concentration of at least about 5 ng/ml.

In another aspect, the invention is directed to a method of treating symptoms of graft-versus-host disease in a subject identified as suffering from graft-versus-host disease, comprising administering to the subject in need thereof a therapeutically effective amount of a population of homogeneous clonal marrow stem cells. The symptom of graft-versus-host disease may be in the gastrointestinal tract, sclerotic skin, limitation of oral intake, dryness of eyes, liver symptoms, shortness of breath, or tightness of arms or legs. The gastrointestinal symptom may be elevated daily volume of stool or inflamed colon. The liver symptom may be raised alkaline phosphatase level in blood serum.

In another aspect, the invention is directed to a method of inhibiting activity of T-cell from donor marrow in a subject identified as suffering from graft-versus-host disease, comprising:

(A) manipulating a biological sample of bone marrow cells, comprising:

(i) allowing the sample of cells to settle in a container;

(ii) transferring supernatant from the container to another container; and (iii) isolating cells from the supernatant, which has comparatively lower density in the sample to obtain a population of homogeneous clonal marrow stem cells; and (B) administering to the subject in need thereof a therapeutically effective amount of the population of homogeneous clonal marrow stem cells obtained in (A).

In the above method, the container may be treated with a coating. The coating may be collagen, poly-lysine, fibrinogen, or gelatin.

In still another aspect, the invention is directed to a method of treating symptoms of graft-versus-host disease in a subject identified as suffering from graft-versus-host disease, comprising:

(A) manipulating a biological sample of bone marrow cells, comprising:

(i) allowing the sample of cells to settle in a container;

(ii) transferring supernatant from the container to another container; and (iii) isolating cells from the supernatant, which has comparatively lower density in the sample to obtain a population of homogeneous clonal marrow stem cells; and (B) administering to the subject in need thereof a therapeutically effective amount of the population of homogeneous clonal marrow stem cells obtained in (A).

A dosage of the cells may be between $1\times10^4$ cell/kg to $1\times10^8$ cell/kg. The cells may express CD29, CD44, and CD105 cell surface antigens, but not HLA-DR cell surface antigens. The cells may express CD29, CD44, CD73 CD90, CD105, and CD166 cell surface antigens but not CD106, CD119, or HLA-DR cell surface antigens. The population of cells may secrete interleukin-10 at a concentration of at least about 5 ng/ml.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
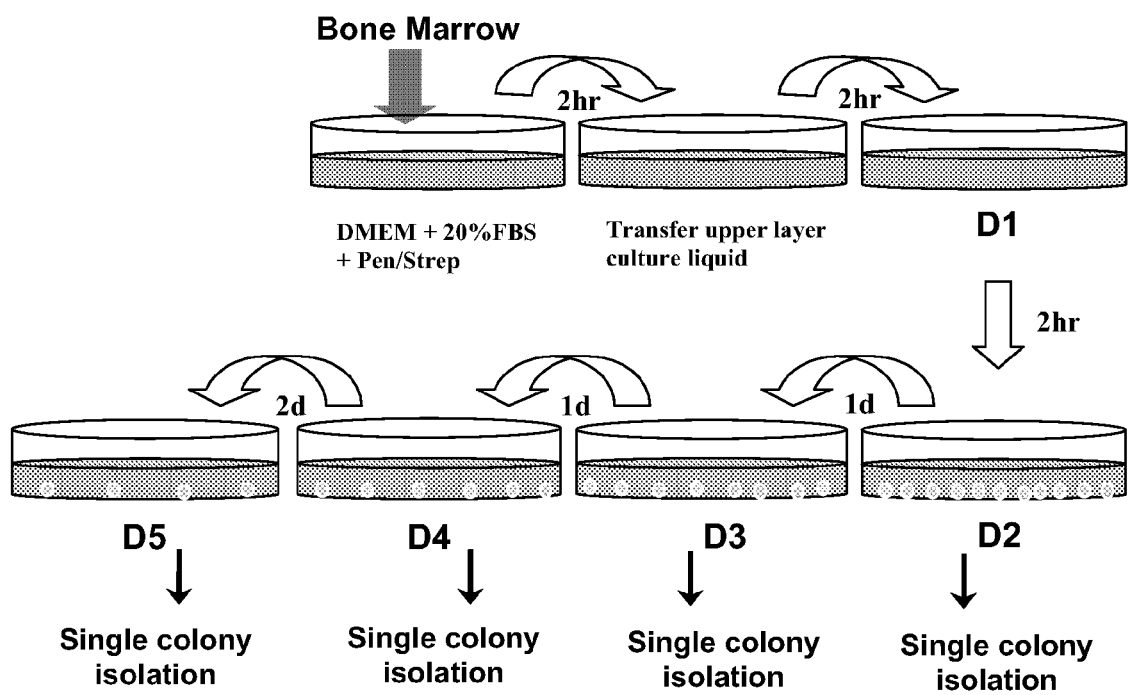
FIG. 1 shows a diagram of the procedure of isolating clonal marrow stem cells or mesenchymal stromal cells by subfractionation culturing method used in this invention.

In the present application, "a" and "an" are used to refer to both single and a plurality of objects.

As used herein, "bodily sample" refers to any sample obtained from a mammal from which is desired to isolate a single type of cell. Such bodily sample includes bone marrow sample, peripheral blood, cord blood, fatty tissue sample, and cytokine-activated peripheral blood.

As used herein, "clonal marrow stem cells" refers to cells that are derived from a single stem cell. This phrase is used interchangeably with "multi-lineage stem cell", which are obtained by subfractionation culturing methods.

As used herein, "homogeneous" population of cells generally indicates that the same type of cells are present within the population. Substantially homogeneous may mean about 80% homogeneity, or about 85%, 90%, 91%, 92%, 93%, 94%, 95%, 96%, 97%, 98%, 99%. 99.1%, 99.2%, 99.3%, 99.4%, 99.5%, 99.6%, 99.7%, 99.8%, or 99.9% homogeneity. In particular, homogeneity of the cells is attributed to the expansion of the cells from a single cell origin. No MSC-specific antigen is currently available and therefore no MSC-specific antibody is available. Theoretically, the only way to obtain 100% homogeneous population of MSCs is to expand a single cell which is identified as a MSC later by characterizing their differentiation and proliferation potentials. The "homogeneous population of stem cells" refers to stem cells that are derived from a single cell identified as a stem cell later by such characterization studies.

As used herein, "lower density cell" refers to cells that have lower density than others in the sample, and are the object of isolation. The lower density cell includes without limitation, multi-lineage stem cells, progenitor cells, other marrow stromal cells.

As used herein, "mammal" for purposes of discussing the source of the cells and treatment refers to any animal classified as a mammal, including humans, domestic and farm animals, and zoo, sports, or pet animals, such as dogs, cats, cattle, horses, sheep, pigs, rats, mice, rabbits, and so on. Preferably, the mammal is human.

As used herein, "MLSC" refers to multi-lineage stem cell.

As used herein, "MLSC/PC" refers to multi-lineage stem cell or progenitor cell.

As used herein, "MSC" refers to marrow stromal cells or mesenchymal stem cells, or marrow stem cells which terms are used interchangeably.

As used herein, "sample of cells" refers to any sample in which is contained a mixture of different types of cells, including bone marrow sample, peripheral blood, cord blood, fatty tissue sample, and cytokine-activated peripheral blood.

Subfractionation Culturing Technique

While not being bound by any particular method of isolating MSC, MLSC or MLSC/PC, a preferred method of obtaining the cells for use in treating Graft Versus Host Disease is by a "subfractionation culturing method", which method is used to isolate a highly homogeneous population of clonal marrow stem cells or multi-lineage stem cells (MLSCs) from a bodily sample or source such as human bone marrow. The procedure is described in U.S. Patent Application Publication US2006/0286669 (Ser. No. 11/471,684, filed Jun. 19, 2006), "Isolation of Multi-Lineage Stem Cells", the contents of which are incorporated herein by reference in their entirety.

Bone marrow MSCs have been known to be difficult to isolate without contamination by hematopoietic cells. For application in clinical settings, it is important to have a homogeneous population of MSCs in order to prevent immunogenic problems and to evaluate the clinical effects correctly. Conventionally, isolation of homogeneous populations of MSCs was carried out by MSC-specific antibody column purification. However, even this method is not adequate as no such perfect MSC-specific antibody is yet available.

In the practice of the subfractionation culturing method, it is not necessary to employ centrifugation of any type to pre-remove any type of cells such as red or white blood cells from the sample because most of the heavier or more dense cells can be removed within the first two, 2-hour incubation steps. Thus, one advantage of the inventive system is that conventionally used density gradient centrifugation and mononuclear cell fractionation steps, which may introduce contamination such as Picoll, Ficoll or Ficoll-hypaque into the cell culture may be avoided. Accordingly, the inventive subfractionation culturing method is a simple, effective, and economic protocol to isolate highly homogeneous MLSCs from a bodily sample, preferably a bone marrow sample.

Alternatively, mononuclear cells isolated/fractionated by conventional density gradient centrifugation method of MSC isolation can also be subjected to the D1 dish to obtain single cell-derived colonies and then to isolate homogeneous populations of stem or progenitor cells (FIG. 1). Therefore, the subfractionation culturing method can be used with the mononuclear cells fractionated by the conventional density gradient centrifugation method.

The present application describes diversity of characteristics in cell surface protein expression of the isolated single-cell derived stem cell lines, which indicates that there are several different types of multi-lineage stem or progenitor cells that exist in biological samples, and in particular bone marrow samples, which are exemplified. The isolated MLSCs were generally negative or dimly positive for CD34, HLA-DR, CD31, CD166, HLA Class I and highly positive for CD44, CD29, CD105. However, some cell lines from D4 and D5 dishes exhibited distinctive levels of surface proteins, which indicates that there could be several different types of multi-lineage stem or progenitor cells in bone marrow (FIG. 1). These MSCs having different surface markers may represent different differentiation potential of the cells. Therefore, isolation of single-cell derived homogeneous stem cells by the subfractionation culturing method makes it possible to isolate tissue-specific stem or committed progenitor cells, as long as these groups of cells exist in the bone marrow or other specifically isolated bodily sample, and culture conditions do not change their potential during cell expansion. The safety and efficacy of MSC treatment and cell engraftment process is improved by being able to characterize subpopulations of cells with specific properties, as shown in the present application.

By eliminating density gradient centrifugation and mononuclear cell fractionation steps and without requiring the use of antibodies to separate stem cells, or particular enzymes, the subfractionation culturing method generates more homogeneous populations of MSCs or MLSCs in a simple, effective, and economic procedure and safer applications for therapeutic settings.

In carrying out the present invention, preferably and without limitation, marrow stem cells may be obtained using the subfractionation culturing method as described above. Further, it is preferable that the obtained MSC's express any or all of CD29, CD44, CD105 cell surface antigens. It is also preferable that any or all of HLA-DR cell surface antigens be not expressed in the MSC's. More preferably, any and all of CD29, CD44, CD90, CD105, and CD166 cell surface antigens are expressed on the MSC's, any or all of the CD106, CD119, and HLA-DR cell surface antigens are not expressed on the MSC's.

Preferably, the inventively used MSC's express Interlukin-10 (IL-10). Preferably, IL-10 is expressed at over 5 ng/ml or over 10 ng/ml after culturing at the time of treatment.

In one aspect, the invention is directed to using cell obtained by the subfractionation culturing method, which includes: 1) the step of obtaining bone marrow from an individual; 2) the step of cultivating the bone marrow; 3) the step of moving only the upper liquid in 2) to a new container and culturing; and 4) the step of separating only the upper liquid of 3) and repeatedly culturing in a culture container that has been optionally treated with coating.

In regards to the above mentioned subfractionation culturing method, while not limited to any particular amount of time, the repeated culturing in the above step 4) may be carried out for about 1 to 4 hours at 37° C. and then repeatedly cultured for about 2 to 3 times for about 12 to 36 hours at 37° C. and then cultured for about 24 to 72 hours at 37° C., and for the upper liquid to be moved to a new culture container each time.

In another aspect, collagen, gelatin, fibrinogen or polylysine-coated culture dishes were used in order to obtain more adherent stem cells. Applicant has discovered that any charged culture surface, either positive or negative, helps the attachment of stem cells to it, compared to the surface of an uncoated dish. More cells were attached to a collagen or polylysine-coated culture dish than uncoated dish, approximately by about two to three fold respectively (data not shown).

Thus, in one embodiment, the bottom of a culture dish can be coated by either positively charged amino acids, such as polylysine, polyarginine, or negatively charged amino acids, such as polyaspartate, polyglutamate, or a combination thereof to help stem or progenitor cells adhere better to the bottom of the dish.

It is preferable that the culture container is treated with a coating, and while any material than can improve the attachment of cells to the container may be used, it is particularly preferred that collagen, poly-lysine, fibrinogen, or gelatin be used. More preferably, collagen or poly-lysine may be used. Even more preferably, collagen may be used. In addition, it is desirable for the cells to be repeatedly cultured for about 3 to 6 times in a culture container that has been treated with collagen and even more desirable for the cells to be repeatedly cultivated about 4 to 5 times.

Pharmaceutical preparation of the therapeutic agent may be made using conventional knowledge in the industry. For example, it can be used in a non oral form of water or a sterilized liquid solution pharmaceutically permissible as well as a suspended injection. For example, pharmaceutical preparation by combining it with a carrier or media that is pharmaceutically permissible, specifically sterile water or a physiological saline solution, vegetable oil, emulsifier, suspensions, surfactant, stabilizer, excipient, vehicle, preservative, binder, and so on, and blending it in a unit capacity format that is generally accepted as being required in a pharmaceutical application can be considered. In addition, sterilized composites for injection can be prescribed based on known pharmaceutical applications using supporting liquids such as injectible distilled water.

For aqueous solutions for injection that can be used jointly, an example can be physiological saline solution, glucose, or isotonic solutions including supportive medications such as D-sorbitol, D-mannose, D-manitol, chloride, or natrium. As for adequate liquefaction supportive agents, an example can be alcohol, specifically ethanol or poly alcohol such as propylene glycol, or a non-ionized surfactant such as polysorbate 80™ or HCO-50.

As an oil agent, sesame oil or soybean oil can be considered and can be used jointly with a benzyl benzoate or benzyl alcohol. In addition, it can be combined with a buffering agent such as phosphate buffering solution, sodium acetate buffering solution, or analgesic solution such as Novocain or stabilizer such as benzyl alcohol, phenol, or antioxidant. The prepared injection liquid is to be charged in a commonly accepted adequate ampoule.

It is desirable for the administration into the body of the patient to be non-oral, and more specifically while it is basic to administer into the vein 1 or 3 times, greater injection is also allowable. Additionally, the administration length can be short or long. More specifically, injection type or transdermal type can be considered. As an example of injection type, while it may be administered through intravenous injection, arterial injection, selectable arterial injection, intramuscular injection, intraperitoneal injection, hypodermic injection, intracerebral injection, cerebral injection, or bone marrow injection, and intravenous injection is desirable. In the case of intravenous injection, because transplantation methods using common blood transfusion have become possible, the patient does not require surgery and furthermore because topical anesthesia is not required, the burden is light on both patient and doctor. When future development of emergency medicine is considered, administration during emergency transportation or at the critical site can be considered.

In addition, this invention provides a method for treating patients with graft-versus-host disease that includes the step of administering mesenchymal or marrow stem cells, in an effective dose for treatment, to the above mentioned patient suffering from graft-versus-host disease.

The effective dose per injection of the clonal marrow cells for treatment of GVHD or the symptoms of GVHD in a mammal and in particular human being may be between $1\times10^4$ cells/kg body weight and $1\times10^8$ cells/kg body weight; between $1\times10^4$ cells/kg body weight and $1\times10^8$ cells/kg body weight; between $2\times10^4$ cells/kg body weight and $1\times10^8$ cells/kg body weight; between $2.5\times10^4$ cells/kg body weight and 1×10⁸ cells/kg body weight; between 2×10⁴ cells/kg body weight and 1×10⁷ cells/kg body weight; between 2.5×10⁴ cells/kg body weight and 1×10⁷ cells/kg body weight; between 2×10⁴ cells/kg body weight and 3×10⁶ cells/kg body weight; between 2.5×10⁴ cells/kg body weight and 3×10⁶ cells/kg body weight; between 2×10⁴ cells/kg body weight and 2×10⁶ cells/kg body weight; between 2.5×10⁴ cells/kg body weight and 2×10⁶ cells/kg body weight; between 2×10⁴ cells/kg body weight and 1×06 cells/kg body weight; between 2.5×10⁴ cells/kg body weight and 1×06 cells/kg body weight; between 2×10⁴ cells/kg body weight and 1×10⁵ cells/kg body weight; or between 2.5×10⁴ cells/kg body weight and 1×10⁵ cells/kg body weight;

Without being limited to any particular administration method, it non oral administration method is preferred. While whole body or partial body administration is possible, whole body administration is preferred and intravenous injection is most preferred.

Treatment of Graft Versus Host Disease

The inventors herein were able to improve the condition of acute or chronic graft-versus-host disease patients who were unresponsive to treatment by administering mesenchymal or marrow stem cells separated using the methods (FIG. 1) described in U.S. Patent Application Publication US2006/0286669, filed Jun. 19, 2006, "Isolation of Multi-Lineage Stem Cells", the contents of which are incorporated herein by reference in their entirety.

As regards the manifestations or symptoms of GVHD, they include sclerotic skin, limitation of oral intake, dryness of eyes, gastrointestinal (GI) tract symptoms such as dysphagia, anorexia, nausea, vomiting, abdominal pain, or diarrhea, liver symptoms as manifested by elevated bilirubin, elevated alkaline phosphatase, and eleveated alanine aminotranferease (ALT)/aspartate aminotransferase (AST) (AST/ALT) ratio, shortness of breath, and/or tightness of arms or legs.

A subject may exhibit multiple symptoms depending on the tissue that is affected by the graft-versus-host disease. Some patients have 4-5 symptoms others may have 1-2 symptoms. Therefore, the present invention is directed to treating any and all of the symptoms associated with GVHD as manifested any tissue in the subject. As the manifestations or symptoms are treated, it is believed that GVHD disease itself is also treated thereby.

The following description provides details of the application of the subfractionation culturing technology and using the homogeneous clonal marrow stem cells obtained thereby to administer to an individual identified as suffering from the symptoms of GVHD. Without being bound by theory, it is believed that the administered stem cells secrete IL-10 in the subject, which counteracts or inactivates the ill effects of the donor's T-cells, thereby treating GVHD and the symptoms of GVHD.

Figure 2:
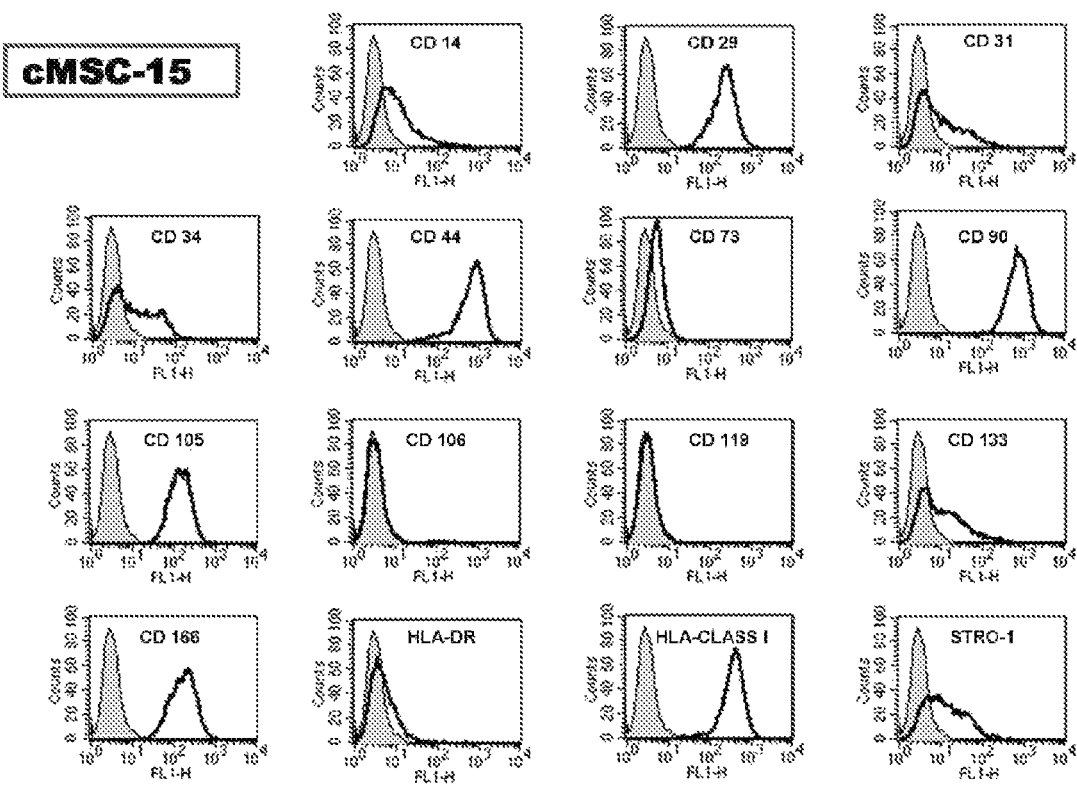
FIG. 2 shows a FACS phenotyping result of cell surface epitopes on the clonal marrow stem cells isolated by subfractionation culturing method and used for the treatment of a GVHD patient.
Figure 3:
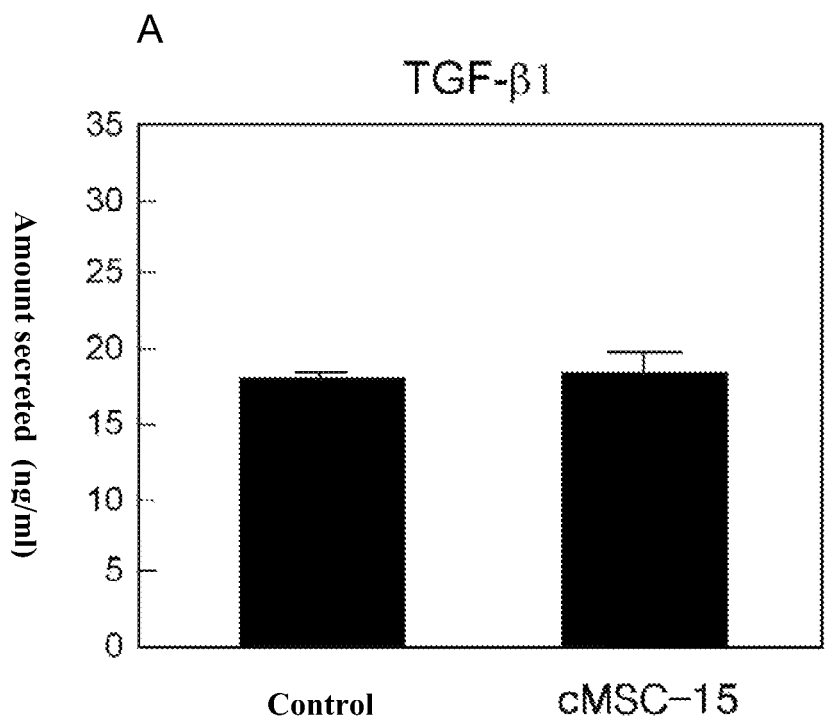
FIGS. 3A-3B show graphs of the amount of (A) TGF-β and (B) IL-10 secreted from the clonal marrow stem cells (cMSC-15) used in the treatment of the GVHD patient and control mesenchymal stem cells isolated by the conventional density gradient centrifugation method.
Figure 3:
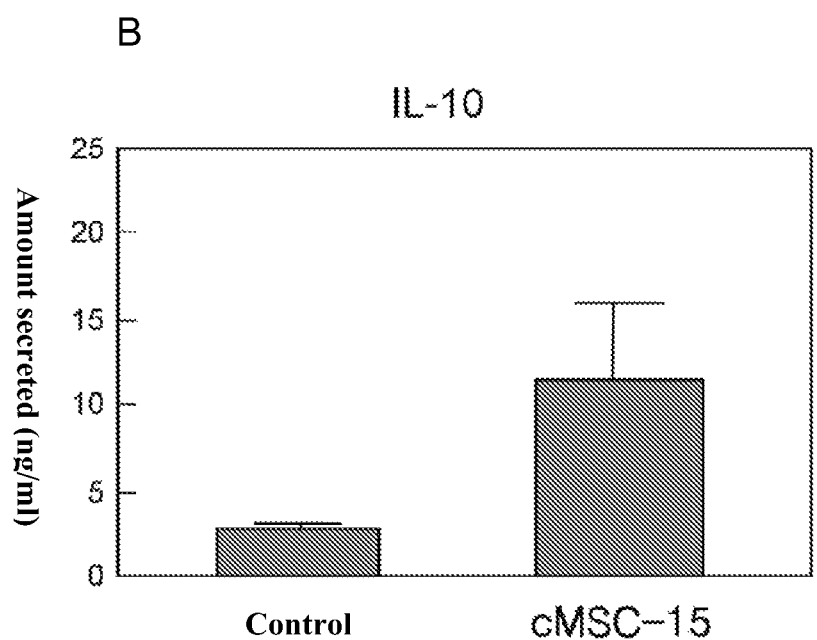

After separating the mesenchymal or marrow stem cell from the mother of the above patient suffering from chronic graft-versus-host disease using the subfractionation culturing method and establishing it as the cell line of monoclonal origin, it was named cMSC-15. A cell surface antigen analysis was carried out through parenchyma cell analysis to determine whether the above cell line was an actual mesenchymal or marrow stem cell (FIG. 2). As a result, because it was shown that CD29, CD44, CD90, CD105, and CD166 cell surface antigens were expressed and CD106, CD119, and HLA-DR cell surface antigens were not expressed, it was confirmed that it was a mesenchymal or marrow stem cell and not a hematopoietic stem cell. CD133 and STRO-1 expression was weakly positive. Accordingly, in order to more specifically verify the characteristics of the above cell line, the degree of expression of TGF-β and IL-10 were verified using the ELISA method (FIG. 3). In the case of TGF-β expression, there was no big difference with the mesenchymal stem cell obtained through conventional density gradient centrifugation method, which is the control. However, IL-10 showed an increase in expression at least 5 times compared with the control.

Accordingly, the inventors herein, after cultivating the above established mesenchymal or marrow stem cell to an amount sufficient for treatment, applied it in the treatment of a patient whose life was in a critical situation due to the onset of chronic graft-versus-host disease. Specifically, the above patient was an 18 year old woman who was diagnosed with acute myelogenous leukemia and after reaching remission through induction therapy, received allogeneic bone marrow transplantation. One month following the stoppage of a six-month administration of immunological suppressants for 6 months, chronic graft-versus-host disease started and while it was treated using Cyclosporine A (CsA), Mycophenolate mofetil (MMF), and steroids, the condition of the patient deteriorated due to continuing hematochezia, increased bilirubin, and dryness of skin, mouth, and eyes, and because of the activation of cytomegalovirus (CMV) due to treatment side effects and BK virus being found even in the urine and blood due to infection of the BK virus, a treatment using Cideforvir was started.

The inventors herein administered the above mentioned cultivated mesenchymal or marrow stem cells through intravenous injection one time after receiving an emergency clinical permit from the Korean Food and Drug Administration. No adverse/negative reactions were observed during or after the administration, and the symptoms of the patient slowly improved after the 1$^{st}$ administration, and a 2$^{nd}$ administration was given after 3 weeks. Afterwards, the patient's symptoms improved and the patient was discharged 34 days after the 2$^{nd}$ administration in a state of having stopped taking steroids and only taking immunological suppressants.

Figure 4:
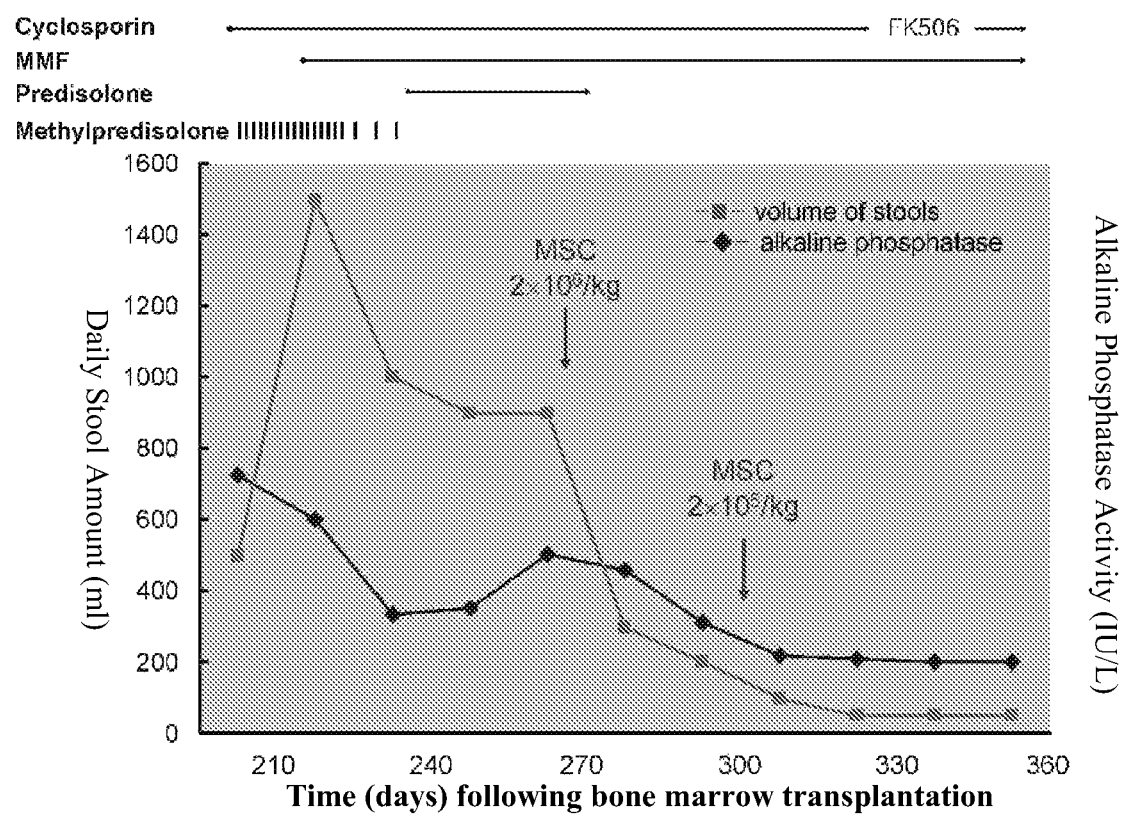
FIG. 4 shows a graph of the changes in the volume of daily stool amount and activity of alkaline phosphatase after the administration of clonal marrow stem cells in the GVHD patient.
Figure 5:
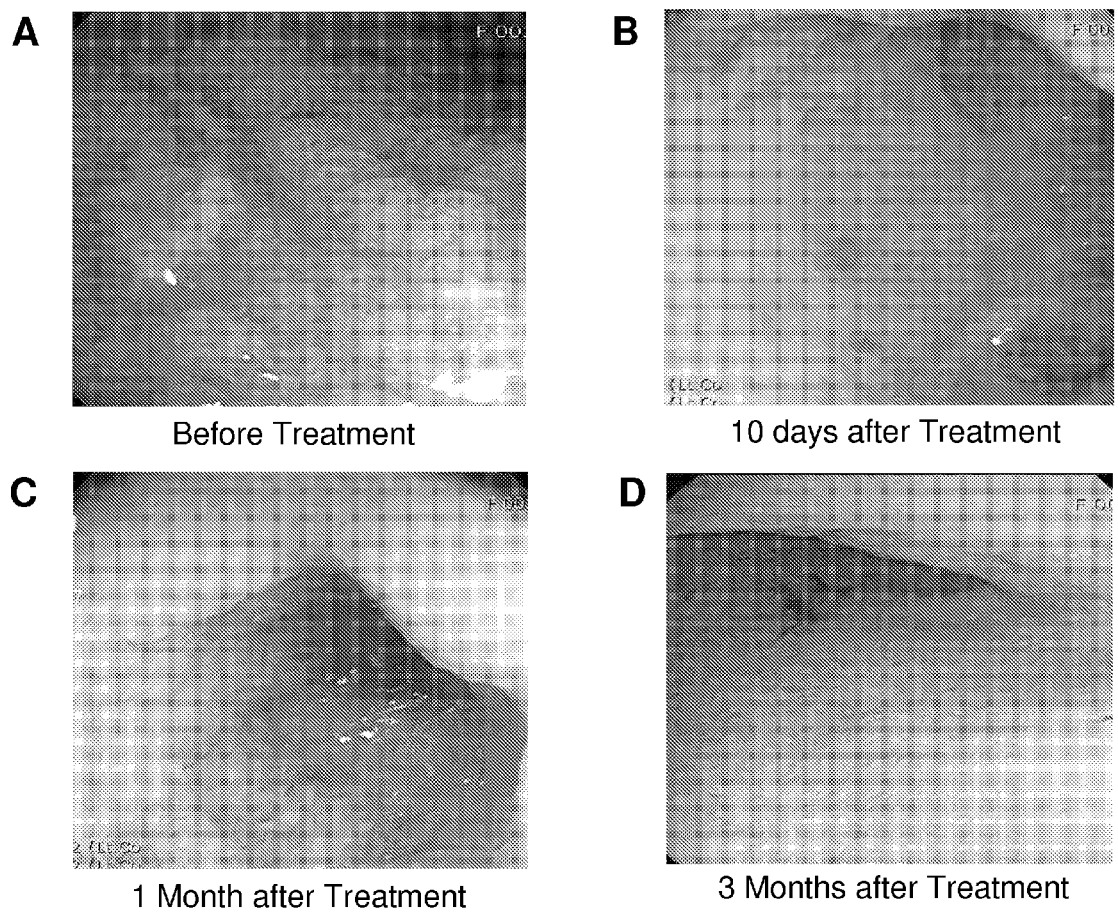
FIGS. 5A-5D show colonoscopy pictures of the GVHD patient who was injected with the clonal marrow stem cells. (A) is a picture prior to treatment, (B) is a picture taken 10 days after treatment, (C) is a picture taken 1 month after treatment, and (D) is a picture taken 3 months after treatment.

In order to verify the pathological effect of the treatment, the inventors herein measured the amount of stool and activity of alkaline phosphatase in the blood, which are major indicators of Graft-Versus-Host-Disease (FIG. 4). The amount of stool had considerably reduced, and the activity of alkaline phosphatase in the blood, which is a serological index had also fallen to normal levels (60-220 ng/ml). In addition, a colonoscopy analysis was carried out to verify whether symptoms had improved (FIG. 5). As can be seen in FIG. 5, with the passage of time following administration of mesenchymal or marrow stem cells in this invention, ulcers had much improved from a colonoscopy data.

As was seen above, the inventors herein verified through clinical trial that mesenchymal or marrow stem cells separated using the subfractionation culturing method of this invention is effective in treating chronic graft-versus-host disease.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Separation of Mesenchymal or Marrow Stem Cells Using Subfractionation Culturing Method After applying local anesthesia to a section of the marrow provider's (mother of treatment target chronic graft-versus-host disease patient) hip, bone marrow was extracted by inserting an injection needle into the hip bone. 15 ml of DMEM (Dulbecco's modified Eagle's Medium, GIBCO-BRL, Life-technologies, MD, USA) which included 20% FBS and 1% penicillin/streptomycin and 2 ml of the marrow extracted from the above mentioned marrow provider was put into a 100 mm culture container and cultivated for 2 hours in a 37° C., 5% $CO_2$ cell cultivator. After cultivation, the culture container was slightly leaned so that the cells attached to the bottom would not fall out and the maximum amount of the upper layer culture liquid in the culture container was moved to a new container.

After repeating the same procedure once more the culture liquid that was taken was moved to a culture container (Becton Dickinson) and cultivated for 2 hours at 37° C. The culture liquid was again moved to a new container and after 24 hours was moved to another new container and after 24 hours was moved to a new container again. Lastly, after 48 hours, it was verified by sight that the cells that were left after moving to a new container were attached and growing on the bottom of the culture container. It can be inferred that the cells that can come to this step having gone through several layered separations are cells that are smaller than the other cells. Once about 3 to 5 hours have passed, the cells form a single clone. This single clone was treated with trypsin, separated, and moved to a 6-well culture container with a cell number of $10^2$ to $6 \times 10^2$ per well. After cultivating for 4 to 5 days in a 37° C., 5% $CO_2$ cell cultivator when it had grown 80%, it was treated with 0.25% trypsin/1 mM EDTA (GIBCO-BRL) and after gathering was moved and successively cultivated in a 75 $cm^2$ culture container. Cell lines with monoclonal origins were acquired as above and named cMSC-15.

As a result of observing the shape of the above cells through a microscope, it was seen that the cells in the initial stage had a shape similar to fibroblast cells and no big changes in the shape were found up to the successive cultivation in stage 5. The time it took for the cells to double was observed to be 24-36 hours, not much different from fibroblast cells.

Example 2

Verification of Separated Mesenchymal or Marrow Stem Cells

Example 2.1

Analysis of Mesenchymal or Marrow Stem Cell Characteristics Using Flow Cytometry In order to verify whether the cMSC-15 cells that were separated from the marrow using the method in the above Example 1 were mesenchymal or marrow stem cells, a flow cytometry (BD Biosciences) was used to find out if cell surface antigens with stem cell characteristics existed.

Stem cells that were successively cultivated for 6 to 7 days in a 75 $cm^2$ culture container was treated with 0.25% trypsin and the cells were gathered. The cells were washed 2 times with a 1×PBS/0.4% BSA to remove trypsin as well as culture liquids. The cells were collected using centrifugal separation and after measuring the number of cells, $1 \times 10^6$ cells were gathered in a 1.5 ml tube and blocked for 1 hour in room temperature using goat serum (Vector). After the completion of blocking, the cells were washed 2 times with a 1×PBS/0.4% BSA and treated with a phycoerythrin (PE) attached anti-CD14, CD29, CD31, CD34, CD44, CD73, CD90, CD105, CD106, CD119, CD133, CD166, HLA-DR, HLA Class 1 and STRO-1 antibody (Serotec Ltd, Kidington, OX, UK) each and reacted for 40 minutes at 4° C. After the cells were washed 2 times with a 1×PBS/0.4% BSA, they were suspended in 0.5 ml 1×PBS/0.4% BSA, loaded in the flow cytometry and analyzed.

CD29, which is an integrin antigen specific for mesenchymal stem cells, as well as CD44 and CD105, which are matrix receptor antigens also specific for mesenchymal stem cells showed a positive reaction. CD90, CD166, and HLA-Class 1 cell surface antigens were expressed, and CD106, CD119, as well as HLA-DR cell surface antigens were not expressed. Aside from this, in the case of CD31, CD133, and STRO-1, an expression level was weakly positive (FIG. 2). Expression of such cell surface antigens was maintained in the cells that has undergone 6 successive cultivations. This indicates that the separated cells, even if they are successively cultivated, the antigens specific for mesenchymal stem cells would be continually expressed.

Example 2.2

Analysis of Cytokine Secretion Condition Related to Mesenchymal Stem Cell's Immunological Suppression The inventors herein, in order to find out more about the characteristics of the isolated mesenchymal stem cells using the subfractionation culturing method in this invention, analyzed the expression levels of immunological suppression related cytokines.

Specifically, after cultivating the mesenchymal or marrow stem cells taken from the same marrow provider and separated using the existing density gradient centrifugation method (control group) and the cMSC-15 in this invention separated using the above mentioned method described in Example 1, the expressed amount of the TGF-β and IL-10 secreted in the culture liquid was analyzed using an enzyme-linked immunosorbent assay (ELISA). For precise analysis, the above two cell lines were cultivated using a serum free batch, and both of the above ELISA used a kit from R&D systems (USA), and was carried out in accordance with the manufacturer's instructions.

As a result of the analysis, while the TGF-β showed little difference from the control group, in the case of the IL-10, the cMSC-15 cells obtained using the subfractionation culturing method showed increased expression over 5 times compared with the control group (FIG. 3). This indicates that there is a correlation between the treatment effectiveness of graft-versus-host disease and the IL-10 expression level of mesenchymal or marrow stem cells.

Example 3

Clinical Application of Isolated Mesenchymal or Marrow Stem Cells

Example 3.1

Administration of Mesenchymal or Marrow Stem Cells

The patient was an 18 year old woman who was diagnosed with acute myelogenous leukemia and after reaching remission through induction therapy, received an allogeneic bone marrow transplantation. One month following the stoppage of a 6-month administration of immunological suppressants, chronic graft-versus-host disease started and while it was treated using Cyclosporine A (CsA), Mycophenolate mofetil (MMF), and steroids, the condition of the patient deteriorated due to continuing hematochezia, increased bilirubin, and dryness of skin, mouth, and eyes, and because of the activation of CMV due to treatment side effects and BK virus being found even in the urine and blood due to infection of the BK virus, a treatment using Cideforvir was started. After receiving an emergency clinical permit from the Korean Food and Drug Administration, the mesenchymal or marrow stem cells of the patient's mother which were isolated as described in Example 1 was cultivated in the GMP facilities and administered to the patient using intravenous injection. No adverse/negative reactions were observed during or after the administration, and the symptoms of the patient slowly improved after the $1^{st}$ administration, and a $2^{nd}$ administration in the same amount as the $1^{st}$ was given after 3 weeks. Afterwards, the patient's symptoms improved considerably and the patient was discharged 34 days after the $2^{nd}$ administration in a state of having stopped taking steroids, left with only taking MMF 1.5 g/day as an immunological suppressant.

Example 3.2

Change in Disease Indicators after Treatment

In order to verify whether the mesenchymal or marrow stem cells isolated using the subfractionation culturing method in this invention is effective for treatment, the inventors herein measured the amount of stool and activity of alkaline phosphatase in the blood which is a major indicator (FIG. 4). The activation of alkaline phosphatase in the blood was accomplished using a commercial kit (Sigma Chemical Company, USA).

As a result, the amount of stool which is a major indicator in chronic graft-versus-host disease was considerably reduced, and the activity of alkaline phosphatase in the blood which is a serological index had also fallen to normal levels (60-220 ng/ml). In addition, a colonoscopy analysis was carried out to verify whether symptoms had improved (FIG. 5). As a result, the colonoscopical opinion at three months following administration of mesenchymal stem cells is that ulcers have been much improved. As has been described, the inventors herein, through clinical trial, have verified that mesenchymal or marrow stem cells separated using the subfractionation culturing method in this invention are effective for treating chronic graft-versus-host disease.

This invention, as it is in regards to a therapeutic agent for treating acute or chronic graft-versus-host disease that includes mesenchymal or marrow stem cells as the active ingredient, the therapeutic agent in this invention can very effectively treat host-versus-host disease which has been very difficult to treat, especially the deadly acute or chronic graft-versus-host disease which occurs frequently as a side effect after bone marrow transplantation surgery.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of treating symptoms of graft-versus-host disease in a subject identified as suffering from graft-versus-host disease, comprising:
    (A) obtaining a homogeneous population of single cell-derived clonal multipotent bone marrow cells based on cell density from a biological sample of bone marrow, comprising:
        (i) allowing the biological sample to settle by gravity in a first container producing a first supernatant of lower density cells;
        (ii) transferring the first supernatant directly without undergoing centrifugation to a second container of growth medium and allowing cells to settle to the bottom producing a second supernatant of lower density cells;
        (iii) transferring the second supernatant directly without undergoing centrifugation to a third container of growth medium and allowing cells to settle to the bottom, producing a third supernatant of lower density cells;
        (iv) transferring the third supernatant directly without undergoing centrifugation to another container of growth medium and allowing cells to settle to the bottom, producing another supernatant of lower density cells;
        (v) allowing single-cell derived colonies to appear on the bottom of the container of step (iv);
        (vi) isolating the single-cell derived colonies; and
        (vii) expanding cells from the single-cell derived colonies in a further other container of growth medium to obtain the homogeneous population of single cell-derived clonal multipotent bone marrow cells, and
    (B) administering to the subject in need thereof a therapeutically effective amount of the homogeneous population of single cell-derived clonal multipotent bone marrow cells obtained in (A) to inhibit T-cell activity from a donor marrow.

2. The method according to claim 1, wherein the cells are settled for one day in step (iv).

3. The method according to claim 1, wherein the isolated cells from the supernatant are expanded in a container.

4. A method of treating symptoms of graft-versus-host disease in a subject identified as suffering from graft-versus-host disease, comprising:
    (A) obtaining a homogeneous population of single cell-derived clonal multipotent bone marrow cells based on cell density from a biological sample of bone marrow, comprising:
        (i) allowing the biological sample to settle by gravity in a first container producing a first supernatant of lower density cells;
        (ii) transferring the first supernatant directly without undergoing centrifugation to a second container of growth medium and allowing cells to settle to the bottom producing a second supernatant of lower density cells;

(iii) transferring the second supernatant directly without undergoing centrifugation to a third container of growth medium and allowing cells to settle to the bottom, producing a third supernatant of lower density cells;

(iv) transferring the third supernatant directly without undergoing centrifugation to a fourth container of growth medium and allowing cells to settle to the bottom, producing a fourth supernatant of lower density cells;

(v) transferring the fourth supernatant directly without undergoing centrifugation to another container of growth medium and allowing cells to settle to the bottom, producing another supernatant of lower density cells;

(vi) allowing single-cell derived colonies to appear on the bottom of the container of step (v);

(vii) isolating the single-cell derived colonies; and (viii) expanding cells from the single-cell derived colonies in a further other container of growth medium to obtain the homogeneous population of single cell-derived clonal multipotent bone marrow cells, and (B) administering to the subject in need thereof a therapeutically effective amount of the homogeneous population of single cell-derived clonal multipotent bone marrow cells obtained in (A) to inhibit T-cell activity from a donor marrow.

5. The method according to claim 4, wherein the cells are settled for one day in step (v).

6. The method according to claim 4, wherein the isolated cells from the supernatant are expanded in a container.

7. A method of treating symptoms of graft-versus-host disease in a subject identified as suffering from graft-versus-host disease, comprising:

(A) obtaining a homogeneous population of single cell-derived clonal multipotent bone marrow cells based on cell density from a biological sample of bone marrow, comprising:

(i) allowing the biological sample to settle by gravity in a first container producing a first supernatant of lower density cells;

(ii) transferring the first supernatant directly without undergoing centrifugation to a second container of growth medium and allowing cells to settle to the bottom producing a second supernatant of lower density cells;

(iii) transferring the second supernatant directly without undergoing centrifugation to a third container of growth medium and allowing cells to settle to the bottom, producing a third supernatant of lower density cells;

(iv) transferring the third supernatant directly without undergoing centrifugation to a fourth container of growth medium and allowing cells to settle to the bottom, producing a fourth supernatant of lower density cells;

(v) transferring the fourth supernatant directly without undergoing centrifugation to a fifth container of growth medium and allowing cells to settle to the bottom, producing a fifth supernatant of lower density cells;

(vi) transferring the fifth supernatant directly without undergoing centrifugation to another container of growth medium and allowing cells to settle to the bottom, producing another supernatant of lower density cells;

(vii) allowing single-cell derived colonies to appear on the bottom of the container of step (vi);

(viii) isolating the single-cell derived colonies; and (ix) expanding cells from the single-cell derived colonies in a further other container of growth medium to obtain the homogeneous population of single cell-derived clonal multipotent bone marrow cells, and (B) administering to the subject in need thereof a therapeutically effective amount of the homogeneous population of single cell-derived clonal multipotent bone marrow cells obtained in (A) to inhibit T-cell activity from a donor marrow.

8. The method according to claim 7, wherein the cells are settled for one day in step (vi).

9. The method according to claim 7, wherein the isolated cells from the supernatant are expanded in a container.

10. A method of treating graft-versus-host disease in a subject identified as suffering from graft-versus-host disease, comprising:

(A) obtaining a homogeneous population of single cell-derived clonal multipotent bone marrow cells based on cell density from a biological sample of bone marrow, comprising:

(i) allowing the biological sample to settle by gravity in a first container producing a first supernatant of lower density cells;

(ii) transferring the first supernatant directly without undergoing centrifugation to a second container of growth medium and allowing cells to settle to the bottom producing a second supernatant of lower density cells;

(iii) transferring the second supernatant directly without undergoing centrifugation to a third container of growth medium and allowing cells to settle to the bottom, producing a third supernatant of lower density cells;

(iv) transferring the third supernatant directly without undergoing centrifugation to another container of growth medium and allowing cells to settle to the bottom, producing another supernatant of lower density cells;

(v) allowing single-cell derived colonies to appear on the bottom of the container of step (iv);

(vi) isolating the single-cell derived colonies; and (vii) expanding cells from the single-cell derived colonies in a further other container of growth medium to obtain the homogeneous population of single cell-derived clonal multipotent bone marrow cells, and (B) administering to the subject in need thereof a therapeutically effective amount of the homogeneous population of single cell-derived clonal multipotent bone marrow cells obtained in (A) to inhibit T-cell activity from a donor marrow.

11. The method according to claim 10, wherein the cells are settled for one day in step (iv).

12. The method according to claim 10, wherein the isolated cells from the supernatant are expanded in a container.

13. A method of treating graft-versus-host disease in a subject identified as suffering from graft-versus-host disease, comprising:

(A) obtaining a homogeneous population of single cell-derived clonal multipotent bone marrow cells based on cell density from a biological sample of bone marrow, comprising:

(i) allowing the biological sample to settle by gravity in a first container producing a first supernatant of lower density cells;

(ii) transferring the first supernatant directly without undergoing centrifugation to a second container of growth medium and allowing cells to settle to the bottom producing a second supernatant of lower density cells;
- (iii) transferring the second supernatant directly without undergoing centrifugation to a third container of growth medium and allowing cells to settle to the bottom, producing a third supernatant of lower density cells;
- (iv) transferring the third supernatant directly without undergoing centrifugation to a fourth container of growth medium and allowing cells to settle to the bottom, producing a fourth supernatant of lower density cells;
- (v) transferring the fourth supernatant directly without undergoing centrifugation to another container of growth medium and allowing cells to settle to the bottom, producing another supernatant of lower density cells;
- (vi) allowing single-cell derived colonies to appear on the bottom of the container of step (v);
- (vii) isolating the single-cell derived colonies; and
- (viii) expanding cells from the single-cell derived colonies in a further other container of growth medium to obtain the homogeneous population of single cell-derived clonal multipotent bone marrow cells, and
- (B) administering to the subject in need thereof a therapeutically effective amount of the homogeneous population of single cell-derived clonal multipotent bone marrow cells obtained in (A) to inhibit T-cell activity from a donor marrow.

14. The method according to claim 13, wherein the cells are settled for one day in step (v).

15. The method according to claim 13, wherein the isolated cells from the supernatant are expanded in a container.

16. A method of treating graft-versus-host disease in a subject identified as suffering from graft-versus-host disease, comprising:
- (A) obtaining a homogeneous population of single cell-derived clonal multipotent bone marrow cells based on cell density from a biological sample of bone marrow, comprising:
  - (i) allowing the biological sample to settle by gravity in a first container producing a first supernatant of lower density cells;
  - (ii) transferring the first supernatant directly without undergoing centrifugation to a second container of growth medium and allowing cells to settle to the bottom producing a second supernatant of lower density cells;
  - (iii) transferring the second supernatant directly without undergoing centrifugation to a third container of growth medium and allowing cells to settle to the bottom, producing a third supernatant of lower density cells;
  - (iv) transferring the third supernatant directly without undergoing centrifugation to a fourth container of growth medium and allowing cells to settle to the bottom, producing a fourth supernatant of lower density cells;
  - (v) transferring the fourth supernatant directly without undergoing centrifugation to a fifth container of growth medium and allowing cells to settle to the bottom, producing a fifth supernatant of lower density cells;
  - (vi) transferring the fifth supernatant directly without undergoing centrifugation to another container of growth medium and allowing cells to settle to the bottom, producing another supernatant of lower density cells;
  - (vii) allowing single-cell derived colonies to appear on the bottom of the container of step (vi);
  - (viii) isolating the single-cell derived colonies; and
  - (ix) expanding cells from the single-cell derived colonies in a further other container of growth medium to obtain the homogeneous population of single cell-derived clonal multipotent bone marrow cells, and
- (B) administering to the subject in need thereof a therapeutically effective amount of the homogeneous population of single cell-derived clonal multipotent bone marrow cells obtained in (A) to inhibit T-cell activity from a donor marrow.

17. The method according to claim 16, wherein the cells are settled for one day in step (vi).

18. The method according to claim 16, wherein the isolated cells from the supernatant are expanded in a container.

* * * * *